(12) United States Patent
Markert

(10) Patent No.: US 6,541,445 B1
(45) Date of Patent: Apr. 1, 2003

(54) UTILIZATION OF TRICYCLIC ALDEHYDES AS ODORIFEROUS AGENTS

(75) Inventor: Thomas Markert, Monheim (DE)

(73) Assignee: Cognis Deutschland GmbH, Duesseldorf (DE)

(*) Notice: Subject to any disclaimer, the term of this patent is extended or adjusted under 35 U.S.C. 154(b) by 0 days.

(21) Appl. No.: 09/673,367

(22) PCT Filed: Apr. 8, 1999

(86) PCT No.: PCT/EP99/03205

§ 371 (c)(1),
(2), (4) Date: Oct. 16, 2000

(87) PCT Pub. No.: WO99/54428

PCT Pub. Date: Oct. 28, 1999

(30) Foreign Application Priority Data

Apr. 17, 1998 (DE) .......................................... 198 17 044

(51) Int. Cl.⁷ ................................................. A61K 7/46
(52) U.S. Cl. ............................... 512/27; 512/8; 512/14; 512/17
(58) Field of Search ............................... 512/17, 8, 14, 512/27

(56) References Cited

U.S. PATENT DOCUMENTS 3,985,769 A    10/1976   Vesley et al.

FOREIGN PATENT DOCUMENTS

DE    26 23 285 A1    12/1977
JP    58/021638       2/1983

OTHER PUBLICATIONS

Patent Abstracts of Japan, vol. 007, No. 095 (C–163), Aug. 23, 1983.
German Translation of JP 58–21638.
A. Spencer, "Hydroformylation of Cyclic Dienes Catalysed by Acetocarbonylbis(Triphenylphosphine)Rhodium (I)", Journal Of Organometallic Chemistry, vol. 124, 1977, pp. 85–91 (XP002116124).

*Primary Examiner*—Jill Warden
*Assistant Examiner*—Monique T. Cole
(74) *Attorney, Agent, or Firm*—John E. Drach; Aaron R. Ettelman

(57) ABSTRACT

The use of tricyclic aldehydes as odorous materials, which can be produced through partial or total hydroformylation of tricyclo[$5.2.1.0^{2,6}$]-dec(adi)enes, except saturated monoaldehydes, is described. The fragrance enhancing capacity of the compounds is described in methods for their use both as perfumes and perfume enhancers or boosters.

14 Claims, No Drawings

UTILIZATION OF TRICYCLIC ALDEHYDES AS ODORIFEROUS AGENTS

FIELD OF THE INVENTION

This invention relates to/the use of special tricyclic aldehydes obtainable by partial or complete hydroformylation of optionally (di)methyl-substituted tricyclo[5.2.1.0$^{2,6}$]dec(adi)enes as perfumes. By "tricyclo[5.2.1.0$^{2,6}$]dec(adi)enes" are meant both tricyclo[5.2.1.0$^{2,6}$]deca-dienes and tricyclo[5.2.1.0$^{2,6}$]decenes. By "(di)methyl-substituted" is meant that the bicyclic system may bear either one or two methyl groups as substituents.

PRIOR ART

The hydroformylation of cyclic dienes is known from the literature. For example, A. Spencer describes the hydroformylation of inter alia 1,3-and 1,5-cyclooctadiene in the presence of special rhodium catalysts in Journal of Organometallic Chemistry 1997, 124, pages 85 to 91. JP 58/21638 describes a process for the production of dialdehydes in which unconjugated diolefins are reacted with hydrogen and carbon monoxide in a water-immiscible solvent in the presence of a rhodium catalyst. Cyclooctane aldehyde (1a)

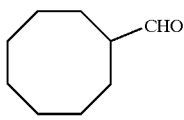

(1a)

is disclosed in U.S. Pat. No. 3,985,769 as a raw material for the production of acetal derivatives with perfume properties, its olfactory properties being described as "intensively green".

Judging by demand, many natural perfumes are available in totally inadequate quantities. Accordingly, it is clear that there is a constant demand in the perfume industry for new perfumes with interesting perfume notes in order to extend the range of naturally available perfumes and to be able to make the necessary adaptations to changing fashion trends and to satisfy the continuously increasing demand for odor enhancers for products of everyday use, such as cosmetics and cleaning products.

In addition, there is generally a constant need for synthetic perfumes which can be favorably produced in a consistent quality and which have desirable olfactory properties, i.e. pleasant, near-natural and qualitatively new odor profiles of adequate intensity, and which are capable of advantageously influencing the fragrance of cosmetic and consumer products. In other words, there is a constant need for compounds which have characteristic new odor profiles coupled with high staying power, intensity of odor and emanative power.

BRIEF SUMMARY OF THE INVENTION

The present invention includes methods of using tricyclic aldehydes obtainable by partial or complete hydroformylation of a tricyclo[5.2.1.0$^{2,6}$]-dec(adi)ene, which may be optionally (di)methyl substituted, excluding saturated monoaldehydes, for providing fragrances to compositions and/or enhancing already existing fragrances. As used herein, "tricyclo[5.2.1.0$^{2,6}$]-dec(adi)ene" includes both tricyclo[5.2.1.0$^{2,6}$]-decadienes and/or tricyclo[5.2.1.0$^{2,6}$]-decenes. Also, as used herein, "(di)methyl-substituted" refers to one or more methyl group substituents located on the bicyclic system of the tricyclo species.

It has surprisingly been found that special tricyclic aldehydes obtainable by partial or complete hydroformylation of optionally (di)methyl-substituted tricyclo[5.2.1.0$^{2,6}$]dec(adi)enes have remarkable olfactory properties. Over and above their special odor characteristic, which is characterized by a broad range with complex nuances, the compounds are distinguished by high staying and emanative power. In addition, they are eminently suitable as perfume boosters. A perfume booster is understood to be a substance which is capable of lastingly intensifying the olfactory impressions of the components of a multicomponent system, i.e. a mixture of two or more perfumes.

The present invention relates to the use of tricyclic aldehydes obtainable by partial or complete hydroformylation of optionally (di)methyl-substituted tricyclo[5.2.1.0$^{2,6}$]dec(adi)enes as perfumes. The compound tricyclo[5.2.1.0$^{2,6}$]decane aldehyde (1b) is excluded. Corresponding to the following formulae, compound (1b) belongs to the following species:

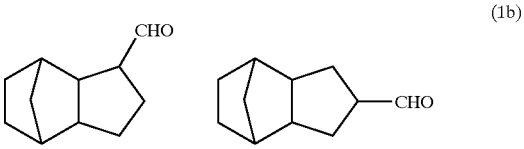

(1b)

The present invention also relates to the use of tricyclic aldehydes obtainable by partial or complete hydroformylation of optionally (di)methyl-substituted tricyclo[5.2.1.0$^{2,6}$]dec(adi)enes, excluding tricyclo[5.2.1.0$^{2,6}$]-decane aldehyde (1b), as perfume boosters. 4,8-diformyl tricyclo[5.2.1.0$^{2,6}$]decane is particularly preferred for this use.

DETAILED DESCRIPTION OF THE INVENTION

The aldehydes to be used in accordance with the invention are advantageously prepared by hydroformylation of optionally (di)methyl-substituted tricyclo[5.2.1.0$^{2,6}$]dec(adi)enes which have a tricyclic system as a common backbone. The backbone is illustrated by formula (2) below, but without any methyl groups or C=C double bonds:

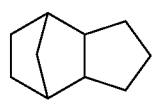

(2)

The system (2) optionally contains one or two methyl groups and compulsorily one or two C=C double bonds. If two C=C double bonds are present, they are not immediately adjacent.

The hydroformylation is a reaction known to the expert which was discovered by Roelen in 1938. In this reaction, alkenes are converted into aldehydes with carbon monoxide and hydrogen. The reaction is also known as oxosynthesis.

If optionally (di)methyl-substituted tricyclo[5.2.1.0$^{2,6}$]dec(adi)enes are used as starting materials for the purposes of the present invention, the hydroformylation may be carried out in part or completely. In the case of partial hydroformylation, one olefinic double bond remains intact per molecule of the starting compound while only the other is hydroformylated; in the case of complete hydroformylation, two CHO groups are introduced into the molecule. If, however, compounds containing only one C=C double bond per molecule are used as starting materials, only complete hydroformylation is of course possible.

The odor profile of the hydroformylation products according to the invention is original and novel. In perfume compositions, they enhance harmony and emanation and also staying power, the particular dosage being adapted to the perfume note required taking the other constituents of the composition into account.

The fact that the hydroformylation products according to the invention have interesting perfume notes was not foreseeable and is confirmation of the general experience that the olfactory properties of known perfumes are not necessarily an indication of the properties of structurally related compounds—in the present case (1a) or (1b) for example—or mixtures thereof because neither the mechanism of odor perception nor the influence of chemical structure on odor perception has been sufficiently researched, i.e. it cannot normally be predicted whether a modified structure or special mixing ratios of known perfumes lead at all to changes in the olfactory properties and whether these changes may be regarded as positive or negative.

By virtue of their odor profiles, the hydroformylation products according to the invention are also particularly suitable for modifying and enhancing known compositions. Particular emphasis is placed above all on their outstanding intensity of odor which contributes quite generally towards the refinement of compositions.

Also remarkable is the way in which the hydroformylation products according to the invention round off and harmonize the perfume notes of a broad range of known compositions without unpleasantly dominating them in any way.

4,8-diformyl tricyclo[5.2.1.0$^{2,6}$]decane (3) is most particularly suitable for use as a perfume and/or perfume booster in accordance with the invention. Accordingly, it is of particular advantage to use 4,8-diformyl tricyclo[5.2.1.0$^{2,6}$]decane in air fresheners for example. In addition, it has been found that 4,8-diformyl tricyclo[5.2.1.0$^{2,6}$]decane may be used with particular advantage for enhancing citrus notes in cleaning compositions.

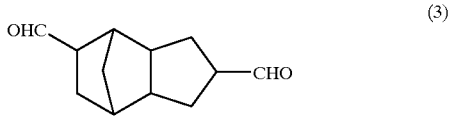

(3)

The quantities in which the hydroformylation products according to the invention are used in perfume compositions are between 0.001 and 70% by weight, based on the mixture as a whole. The hydroformylation products according to the invention and corresponding compositions may be used both for perfuming cosmetic preparations, such as lotions, creams, shampoos, soaps, salves, powders, aerosols, toothpastes, mouthwashes, deodorants, and in extract perfumery. They may also be used for perfuming technical products and detergents and cleaning compositions, fabric softeners, textile treatment compositions and tobacco. For perfuming these various products, the compositions are added to them in an olfactorily effective quantity, more particularly in a concentration of 0.05 to 2% by weight, based on the product as a whole. However, these values are not intended to represent limits because the experienced perfumist can still obtain effects with lower concentrations or can build up new complexes with even higher concentrations.

The following Examples are intended to illustrate the invention without limiting it in any way.

EXAMPLES

1. Preparation of 4,8-diformyl tricyclo[5.2.1.0$^{2,6}$] decane (3)

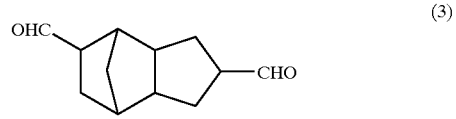

(3)

2 Moles (264.4 g) of dicyclopentadiene (manufacturer: Acros; gas chromatographic purity: 95%) were introduced into an autoclave together with 1.7 mmoles (1.175 g) of a rhodium catalyst with the formula Rh(CO)Cl(PPh$_3$)$_2$ and 19 mmoles (5 g) of triphenyl phosphine and reacted with a 1:1 mixture of hydrogen and carbon monoxide with intensive stirring for 5 hours at 100° C. under a pressure of 60 kg/cm$^2$ and in the absence of solvent. For working up, the contents of the reactor were filtered and distilled through a 20 cm Vigreux column.

Fractionation into educt, monoaldehyde and dialdehyde was carried out in a spinning band column. 118.6 g of a mixture of 2,8-, 3,8- and 4,8-diformyl tricyclo[5.2.1.0$^{2,6}$] decane (boiling point: 65–75° C./0.07 mbar) were obtained.

Odor description: spruce note.

What is claimed is:

1. A method of providing a fragrance to a composition, said method comprising:
    (a) providing a composition; and
    (b) adding a fragrance-providing effective amount of a tricyclic aldehyde to the composition, wherein the tricyclic aldehyde is prepared by hydroformylation of a tricyclo[5.2.1.0$^{2,6}$]-dec(adi)ene, with the proviso that the tricyclic aldehyde is not a saturated monoaldehyde.

2. The method according to claim 1, wherein the tricyclic aldehyde comprises 4,8-diformyl tricyclo[5.2.1.0$^{2,6}$]-decane.

3. The method according to claim 1, wherein the tricyclic aldehyde is added in an amount of from about 0.001 to about 70% by weight, based on the combined weight of the composition and the tricyclic aldehyde.

4. The method according to claim 2, wherein the tricyclic aldehyde is added in an amount of from about 0.001 to about 70% by weight, based on the combined weight of the composition and the tricyclic aldehyde.

5. The method according to claim 1, wherein the tricyclic aldehyde is prepared by hydroformylation of a tricyclo [5.2.1.0$^{2,6}$]-dec(adi)ene at a temperature of about 100° C. and at a pressure of about 60 kg/cm$^2$.

6. The method according to claim 1, wherein the composition is selected from the group consisting of cosmetic preparations, detergents, cleaning compositions, fabric softeners, textile treatment compositions, alcohol-based perfumes and tobacco.

7. The method according to claim 2, wherein the composition is selected from the groups consisting of cosmetic preparations, detergents, cleaning compositions, fabric softeners, textile treatment compositions, alcohol-based perfumes and tobacco.

8. A method of enhancing fragrance characteristics of a composition, said method comprising:
    (a) providing a composition comprising one or more fragrant components;

(b) providing a tricyclic aldehyde to the composition, wherein the tricyclic aldehyde is prepared by hydroformylation of a tricyclo[5.2.1.0$^{2,6}$]-dec(adi)ene, with the proviso that the tricyclic aldehyde is not a saturated monoaldehyde; and (c) combining the composition and a fragrance-enhancing effective amount of the tricyclic aldehyde.

9. The method according to claim 8, wherein the tricyclic aldehyde comprises 4,8-diformyl tricyclo[5.2.1.0$^{2,6}$]-decane.

10. The method according to claim 8, wherein the tricyclic aldehyde is added in an amount of from about 0.001 to about 70% by weight, based on the combined weight of the composition and the tricyclic aldehyde.

11. The method according to claim 9, wherein the tricyclic aldehyde is added in an amount of from about 0.001 to about 70% by weight, based on the combined weight of the composition and the tricyclic aldehyde.

12. The method according to claim 8, wherein the tricyclic aldehyde is prepared by hydroformylation of a tricyclo[5.2.1.0$^{2,6}$]-dec(adi)ene at a temperature of about 100° C. and at a pressure of about 60 kg/cm$^2$.

13. The method according to claim 8, wherein the composition is selected from the group consisting of cosmetic preparations, detergents, cleaning compositions, fabric softeners, textile treatment compositions, alcohol-based perfumes and tobacco.

14. The method according to claim 9, wherein the composition is selected from the groups consisting of cosmetic preparations, detergents, cleaning compositions, fabric softeners, textile treatment compositions, alcohol-based perfumes and tobacco.

* * * * *